United States Patent [19]

Scherberich

[11] 4,153,606

[45] May 8, 1979

[54] PROCESS FOR THE PRODUCTION OF THIAZOLINE-(3) COMPOUNDS

[75] Inventor: Paul Scherberich, Dietzenbach, Fed. Rep. of Germany

[73] Assignee: Deutsche Gold- und Silber-Scheideanstalt vormals Roessler, Frankfurt, Fed. Rep. of Germany

[21] Appl. No.: 840,714

[22] Filed: Oct. 11, 1977

[30] Foreign Application Priority Data

Oct. 9, 1976 [DE] Fed. Rep. of Germany ....... 2645731

[51] Int. Cl.² ........................................ C07D 277/08
[52] U.S. Cl. ........................................... 260/306.7 R
[58] Field of Search ............................... 260/306.7 R

[56] References Cited

U.S. PATENT DOCUMENTS

| | | | |
|---|---|---|---|
| 3,004,981 | 10/1961 | Asigner et al. | 260/306.7 |
| 3,700,683 | 10/1972 | Asigner et al. | 260/306.7 R |
| 3,931,208 | 1/1976 | Offermanns et al. | 260/306.7 R |

FOREIGN PATENT DOCUMENTS

| | | |
|---|---|---|
| 1063602 | 8/1939 | Fed. Rep. of Germany. |
| 1795299 | 3/1972 | Fed. Rep. of Germany. |

OTHER PUBLICATIONS

Asinger et al., Angewandte Chemie, International Edition 6, 1967 (907–919).

*Primary Examiner*—Nicholas S. Rizzo

*Attorney, Agent, or Firm*—Cushman, Darby & Cushman

[57] ABSTRACT

Thiazoline-(3) compounds of the formula

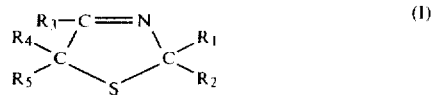

(I)

in which $R_1$, $R_2$, $R_3$, $R_4$ and $R_5$ are hydrogen, alkyl, alkenyl, cycloalkyl, cycloalkenyl, aryl, alkaryl or aralkyl or $R_1$ and $R_2$ or $R_3$ and $R_4$ or $R_3$ and $R_5$ or $R_4$ and $R_5$ are joined together to form a saturated or unsaturated ring are prepared by reacting (1) an oxo compound having a halogen atom on the carbon adjacent to the carbonyl group and having the formula

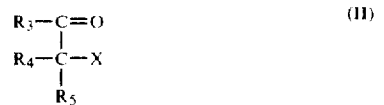

(II)

where X is halogen, (2) an oxo compound of the formula

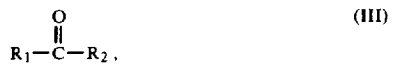

(III)

(3) a metal or ammonium sulfide and (4) ammonia.

14 Claims, No Drawings

PROCESS FOR THE PRODUCTION OF THIAZOLINE-(3) COMPOUNDS

BACKGROUND OF THE INVENTION

The invention is directed to a process for the production of thiazoline-(3) compounds from oxo compounds, sulfur compounds and ammonia. Thiazoline-(3) compounds serve as oxidation inhibitors for polyolefins. They are also starting materials for the production of sulfur containing amino acids such as cysteine and penicillamine.

It is known to produce 2,5,5-trialkyl substituted thiazoline-(3) compounds by reacting alkylidene vinyl amines with sulfur (Schade German Auslegeschrift No. 1,063,602), or by reaction of an aldehyde branched on the α-carbon atom with sulfur and ammonia (German Offenlegungsschrift No. 1,795,299 and related Asinger U.S. Pat. No. 3,700,683). It is also known that thiazoline-(3) compounds having alkyl substituents in the 2, 4 and 5 positions are formed by reacting ketones which have at least one hydrogen atom in the α-position to the oxo group with sulfur and ammonia (Asinger, Angewandte Chemie, International Edition 6 (1967) 907–919, particularly page 908). This process in some cases only results in moderate yields. Besides, according to this process only certain thiazoline-(3) compounds can be recovered. Thiazolines which are not substituted in the 2- or 5-position or in 2-, 4- or 5-position are not accessible by this process.

Besides, it is known to produce thiazoline-(3) in a given case substituted in the 2, 4 and 5 positions by reaction of α-mercaptoaldehydes, α-mercaptoketones or S-acetylated α-mercaptoketones with oxo compounds and ammonia (Asinger, Angewandte Chemie, loc. cit., particularly pages 909 to 910). There are produced thiazoline-(3) compounds, in a given case substituted in the 2, 4 and 5 positions from 2,2-dioxodisulfides, oxo compounds, ammonia and hydrogen sulfide (Asinger U.S. Pat. No. 3,004,981) or there are produced 2 and 5 position substituted thiazoline-(3) compounds by such process (Offermanns German OS No. 2,254,701 and related Offermanns U.S. Pat. No. 3,931,208). The disadvantage of this process is that it is required starting materials which are not readily accessible.

SUMMARY OF THE INVENTION

There has now been found a process for the production of thiazolines-(3) from oxo compounds, sulfur compounds and ammonia characterized by reacting oxo compounds which are substituted on the carbon atom adjacent to the oxo group by a halogen with oxo compounds, metal sulfides and ammonia. According to this process the thiazoline-(3) is recovered from relatively easily accessible starting materials. While the known processes are suited in part for the production of thiazolines substituted in specific positions, according to the process of the invention there can be produced unsubstituted thiazoline-(3) or thiazoline-(3) substituted in the 2-, 4- and/or 5-position with outstanding yields.

According to the invention there are produced thiazoline-(3) compounds of the formula

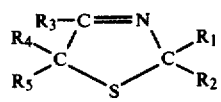
(I)

in which $R_1$, $R_2$, $R_3$, $R_4$ and $R_5$ are the same or different and are hydrogen or straight or branched chain alkyl groups with preferably 1 to 18 and especially 1 to 8 carbon atoms or, straight or branched chain alkenyl groups with preferably 2 to 8 and especially 2 to 6 carbon atoms or, where $R_1$ and $R_2$ or $R_3$ and $R_4$ or $R_3$ and $R_5$ or $R_4$ and $R_5$ can also be joined to form a closed saturated or unsaturated ring (i.e., including the adjacent carbon atom or carbon atoms of the thiazoline ring), with preferably 3 to 12 and particularly 4 to 7 carbon atoms, or cycloalkyl groups with preferably 3 to 12 and particularly 5 to 8 carbon atoms, or cycloalkenyl groups with preferably 3 to 12 and particularly 5 to 8 carbon atoms, or aryl groups, or alkaryl groups with preferably 1 to 6 and particularly 1 to 2 carbon atoms in each alkyl group, or aralkyl groups with preferably 1 to 6 and particularly 1 to 2 carbon atoms in each alkyl group by reacting (1) an oxo compound of the formula

(II)

where $R_3$, $R_4$ and $R_5$ are defined as in formula (I) and X is a halogen preferably chlorine or bromine with (2) an oxo compound of the formula

(III)

where $R_1$ and $R_2$ are as defined in formula (I) with (3) an ammonium or metal sulfide and (4) ammonia.

Illustrative of compounds within formula (I) that can be prepared according to the invention are thiazoline-(3); 2,2,5,5-tetramethyl thiazoline-(3); 2,2-pentamethylene-5,5-dimethyl thiazoline-(3); 2,2-diethyl-5,5-dimethyl thiazoline-(3); 2-benzyl-5,5-dimethyl thiazoline-(3); 2,2-dimethyl-5,5-pentamethylene thiazoline-(3); 2,2-dimethyl-5,5-heptamethylene thiazoline-(3); 2-methyl-2-propyl-5-ethyl-5-butyl thiazoline-(3); 2,2,5,5-tetraethyl thizaoline-(3); 2,2-dihexyl-5,5-dimethyl thiazoline-(3); 2-methyl-2-isopropyl-5,5-dipropyl thiazoline-(3); 2-methyl-2-ethyl-5,5-diisopropyl thiazoline-(3); 2-isopropyl-5,5-dimethyl thiazoline-(3); 2,2,5-trimethyl-5-amyl thiazoline-(3); 2,5,5-trimethyl-2-hexyl thiazoline-(3); 2-allyl-2,5,5-trimethyl thiazoline-(3); 2-butenyl-2-methyl-5,5-diethyl thiazoline-(3); 2,5-dimethyl-2-ethyl-5-butenyl thiazoline-(3); 2-phenethyl-5,5-dimethyl thiazoline-(3); 2.2-dimethyl-5-benzyl-5-ethyl thiazoline-(3); 2,2,5-trimethyl-5-phenethyl thiazoline-(3); 2-phenpropyl-2,2,5-trimethyl thiazoline-(3); 2,2,5,5-di(pentamethylene)-thiazoline-(3); 2,2-pentamethylene-5,5-hexa-methylene thiazoline-(3); 2,2-heptamethylene-5-methyl-5-ethyl thiazoline-(3); 2,2-dimethyl-5,5-octamethylene thiazoline-(3); 2,2-dodecamethylene-5,5-dimethyl thiazoline-(3); 2,2-dimethyl-5,5-undecamethylene thiazoline-(3); 2,4,5-trimethyl-2-ethyl thiazoline-(3); 2,2-pentamethylene-4-ethyl-5-methyl thiazoline-(3); 2,2,4-triethyl-5-methyl thiazoline-(3); 2-ethyl-4-methyl thiazoline-(3); 2,5-diethyl-4-n-propyl thiazoline-(3); 2,5,5-trimethyl-4-isopropyl thiazoline-(3); 2-ethyl-4-phenyl thiazoline-(3); 2,2,4-trimethyl-5-phenyl thiazoline-(3); 2,2-pentamethylene-4,5-tetramethylene thiazoline-(3); 2,2-diethyl-4-methyl-5,5-pentamethylene thiazoline-(3); 2,2-pentamethylene-4-cyclohexyl thiazoline-(3); 2-ethyl-4-t-butyl thiazoline-(3); 2-methyl-2,4-dibenzyl thiazoline-(3); 2-isopropyl-4-ethyl-5-methyl thiazoline-(3); 2-cyclohexyl-4-ethyl-5-methyl thiazoline-(3); 2-isopropyl-5,5-dimethyl thiazoline-(3); 2,5-dimethyl-2-n-octyl thiazoline-(3); 2-isooctyl thiazoline-(3); 2,2-dimethyl-4,5-di-n-octyl thiazoline-(3); 2-crotyl-5,5-dimethyl thiazoline-(3); 2,2-dimethyl-5-vinyl thiazoline-(3); 2-hexenyl-5,5-dimethyl thiazoline-(3); 2,2-dimethyl-4,5-octamethylene thiazoline-(3); 2,4,5,5-tetramethyl-2-cyclopentyl thiazoline-(3); 2,5,5-trimethyl-2-cyclohexenyl thiazoline-(3); 2-p-tolyl thiazoline-(3); 2,4,5-trimethyl-2-o-tolyl thiazoline-(3); 2,2-dimethyl-5-p-ethylphenyl thiazoline-(3); 2,5-dimethyl-2-p-butylphenyl thiazoline-(3); 2-methyl-2-p-hexylphenyl thiazoline-(3).

As oxo compounds of formula (II) which have the carbon atom adjacent to the oxo group substituted by halogen, there can be used for example chloroacetaldehyde, 2-chloropropanal-(1); 2-chloro-n-butanol-(1); 2-chloro-2-methylpropanal-(1); 2-chloro-n-butanal-(1); 2-chloro-2-methylpropanal-(1); 2-bromo-n-pentenal-(1); 2-chloro-2-methylbutanal-(1); chloroacetone,2-chlorobuten-(2)-al-(1); phenyl acyl bromide; 1-phenyl-3-chloropropanone-(2); 2-bromobutanone-(3); 2-chlorocyclopentanone-(1); 2-chlorocyclohexanone-(1); 2-chlorocyclooctanone-(1); 2-chlorocyclododecanone-(1); phenacyl chloride; phenacyl iodide; 2-bromoacetaldehyde; bromoacetaldehyde; 2-chloro-n-nonanal-(1); 2-chloro-n-octadecanal-(1); 2-chloro-n-nonadecanal-(1); 2-chloro-propan-(1); 2-chloro-propen-(2)-al-(1); 1-phenyl-2-chloropropanone-(2); 2-chloro-1-phenyl acetaldehyde; 2-chloro-1-p-tolyl acetaldehyde; 2-chloro-1-o-ethylphenyl acetaldehyde; 2-chloro-1-benzyl acetaldehyde; 2-chloro-1-phenethyl acetaldehyde; 2-methyl-2-chlorocyclopentanone; 2-methyl-cyclododecanone-(1); 2-hexyl-cyclohexanone-(1); 2-chlorohexen-(2)-al-(1); 9-chlorooctadecanone-(8); 2-chloropentanone-(3); 3-chlorodecanone-(2).

As oxo compounds of formula (III) there can be used for example acetaldehyde; propionaldehyde; n-butyraldehyde; cyclopentanealdehyde; cyclohexanealdehyde; cyclooctanealdehyde; cyclododecanaldehyde; valeraldehyde; hexanealdehyde; heptanealdehyde; 2-phenylacetaldehyde; 3-phenyl-propionaldehyde; 4-phenylbutyraldehyde; isobutyraldehydel sec.-valeraldehyde; acrolein; crotonaldehyde; Δ-6-hexenaldehyde; acetone; methyl ethyl ketone; diethyl ketone; methyl isobutyl ketone; heptanone-4-phenylacetone; pentanone-2; cyclopentanone; cyclohexanone, dibenzyl ketone; cyclooctanone; cyclododecanone; methyl heptyl ketone; dibutyl ketone; di sec.butyl ketone; diisobutyl ketone; divinyl ketone; diallyl ketone; methyl hexen-1-yl ketone; dimethallyl ketone; methyl vinyl ketone; ethyl vinyl ketone; methyl allyl ketone; methyl butene-1-yl ketone; cyclohexanealdehyde; cyclopentanealdehyde; diethyl ketone; mesityl oxide; phorone; 2-methyl cyclohexanone-(1); acetaphenone; propiophenone; diphenyl ketone; capraldehyde; pelargonaldehyde; lauraldehyde; stearaldehyde; citronellal; benzaldehyde; p-tolualdehyde; di-n-undecyl ketone; di-n-heptadecyl ketone; cinnamaldehyde; methyl n-octadecyl ketone; methyl n-amyl ketone; di-n-propyl ketone; diisopropyl ketone; methyl n-hexyl ketone; methyl n-nonyl ketone; methyl isopropenyl ketone; methyl propenyl ketone; 3-heptenone-(2); crotylidene acetone; phenyl vinyl ketone and phenyl propenyl ketone.

As metal sulfides there are chiefly employed those which have good solubility in water. For example, these include the hydrogen sulfides of alkaline earth metals and alkali metals. Particularly suited are ammonium hydrogen sulfide and alkaline earth hydrogen sulfides, e.g., calcium hydrogen sulfide and barium hydrogen sulfide and the alkali hydrogen sulfides, especially potassium hydrogen sulfide and sodium hydrogen sulfide.

The ammonia can be added as such or as Diverssche solution ($NH_4NO_3.2NH_3$).

The proportions are not critical and can be varied widely. Thus, they can be either stoichiometric, below stoichiometric or over stoichiometric. Generally, however, it is suitable based on the halogen substituted oxo compound (II) to add at least stoichiometric amounts of oxo compound (III), metal (or ammonium hydrogen sulfide and ammonia. Preferably per mole of the halogen substituted oxo compound (II) there are used about 1 to 2 moles of oxo compound (III), an amount of metal or ammonium sulfide corresponding to 1 to 2 gram atoms of sulfur and 2 to 3 moles of ammonia.

The materials are brought to reaction either undiluted or diluted by a solvent. As solvents there can be used water or organic liquids or mixtures thereof. As organic solvents there can be used for example lower alkanols such as methanol, ethanol and propanol-(2), saturated aliphatic hydrocarbons such as gasoline fractions, aromatic hydrocarbons such as benzene, toluene and xylene, ethers such as diethyl ether, and halogenated hydrocarbons such as chloroform, carbon tetrachloride, methylene chloride and chlorobenzene. The solvent is in a given case partially or completely introduced with the reacting materials as solutions in the solvents employed.

Although the materials can in general be brought together in any sequence it is preferably to have the oxo compound (III) present in admixture with the metal or ammonium sulfide and to simultaneously introduce into this mixture the halogen substituted oxo compound (II) and the ammonia.

The reaction temperature in a given case is adjusted according to the type of solvent, the type of reacting materials and the proportions. Generally it is suitable to choose temperatures between −10° C. and the boiling point of the reaction mixture. In most cases preferably the temperatures are between about 0° and 50° C.

Unless otherwise indicated all parts and percentages are by weight.

The process can comprise, consist essentially of or consist of the stated steps and materials.

DESCRIPTION OF THE PREFERRED EMBODIMENTS

EXAMPLE 1

There was present a suspension of 67 grams (1.2 moles) of sodium hydrogen sulfide in 110 grams (1.5 moles) of 2-methylpropanal-(1). Into this there were dropped in 106 grams (1.0 mole) of 2-chloro-2-methylpropanal-(1) and simultaneously ammonia was led in. The temperature was held at 15° to 25° C. by cooling. The introduction of ammonia was continued as long as the development of heat continued in the reaction mixture. The 2-isopropyl-5,5-dimethylthiazoline-(3) formed was recovered from the reaction mixture by fractional distillation. Its boiling point was 68° to 72° C. at 16 mbar. The yield amounted to 120 grams, corresponding to 76% based on the 2-chloro-2-methylpropanal-(1) added.

EXAMPLE 2

The procedure was the same as in Example 1 except there were employed 120 grams (1.4 moles) of diethyl ketone with 80 grams (1.1 moles) of potassium hydrogen sulfide and 106 grams (1.0 mole) of 2-chloro-2-methylpropanal-(1) and ammonia. The yield of 2,2-diethyl-5,5-dimethylthiazoline-(3) amounted to 135 grams, corresponding to 79% based on the 2-chloro-2-methylpropanal-(1) employed. The thiazoline had a boiling point of 50° to 52° C. at 1.3 mbar.

EXAMPLE 3

The procedure was the same as in Example 1 except there were employed 70 grams (1.2 moles) of propionaldehyde, 80 grams (1.1 moles) of potassium hydrogen sulfide and 137 grams (1.0 mole) of bromoacetone and ammonia. The yield of 2-ethyl-4-methyl-thiazoline-(3) amounted to 90 grams, corresponding to 70% based on the bromoacetone employed. The thiazoline had a boiling point of 59° to 63° C. at 7 mbar.

EXAMPLE 4

The procedure was the same as in Example 1 except there were employed 70 grams (1.2 moles) of propionaldehyde, 58 grams (1.0 mole) of sodium hydrogen sulfide and 199 grams (1.0 mole) of phenacyl bromide with ammonia. The 2-ethyl-4-phenyl-thiazoline-(3) recovered was purified by recrystallization from methanol. It had a melting point of 50° to 52° C. The yield was 140 grams, corresponding to 73% based on the phenacyl bromide (2-bromoacetophenone) employed.

EXAMPLE 5

The procedure was the same as in Example 1 except there were employed 90 grams (1.6 moles) of acetone, 67 grams (1.2 moles) of sodium hydrogen sulfide and 151 grams (1.0 mole) of 2-bromo-2-methylpropanal-(1) with the ammonia. The yield of 2,2,5,5-tetramethyl-thiazoline-(3) was 110 grams, corresponding to 77% based on the 2-bromo-2-methylpropanal-(1). The thiazoline had a melting point of 50° to 52° C.

EXAMPLE 6

The procedure was the same as in Example 1 except that there were employed 87 grams (1.5 moles) of acetone, a solution of 67 grams (1.2 moles) of sodium hydrogen sulfide in 100 ml of water and 175 grams of a 45 percent aqueous solution of chloroacetaldehyde (1.0 mole) with the ammonia. The 2,2-dimethyl-thiazoline-(3) formed separated out of the reaction mixture as an oil. It was separated and fractionally distilled. Its boiling point was 40° to 45° C. at 16 mbar. The yield was 85 grams, corresponding to 74% based on the chloroacetaldehyde employed.

EXAMPLE 7

The procedure was the same as in Example 1 except there were employed 130 grams (1.5 moles) of diethyl ketone, a solution of 67 grams (1.2 moles) of sodium hydrogen sulfide in 100 ml of water and 175 grams of a 45 percent aqueous solution of chloroacetaldehyde (1.0 mole) with the ammonia. The yield of 2,2-diethyl-thiazoline-(3) was 100 grams, corresponding to 70% based on the chloroacetaldehyde employed. The thiazoline had a boiling point of 77° to 80° C. at 16 mbar.

EXAMPLE 8

The procedure was the same as in Example 1 except that there were employed 120 grams (1.2 moles) of cyclohexanone, a solution of 80 grams (1.1 moles) of potassium hydrogen sulfide in 100 ml of water and 105 grams of a 75 percent aqueous solution of chloroacetaldehyde (1.0 mole) with the ammonia. The yield of 2,2-pentamethylenethiazoline-(3) was 115 grams, corresponding to a yield of 73%, based on the chloroacetaldehyde employed. The thiazoline had a boiling point of 100° to 105° C. at 16 mbar.

EXAMPLE 9

The procedure was the same as in Example 1 except that there were employed 110 grams (1.5 moles) of butanone-(2), a solution of 80 grams (1.1 moles) of potassium hydrogen sulfide in 100 ml of water and 175 grams of a 45 percent aqueous solution of chloroacetaldehyde (1.0 mole) with the ammonia. The yield of 2-methyl-2-ethyl-thiazoline-(3) was 112 grams, corresponding to 80%, based on the chloroacetaldehyde employed. The thiazoline had a boiling point of 52° to 55° C. at 16 mbar.

EXAMPLE 10

There were present a mixture of 151 grams (1.0 mole) of 3-bromobutanone-(2), 110 grams (1.1 mole) of cyclohexanone and 300 ml of methylene chloride. At temperatures between 15° and 20° C. there were dropped in a solution of 67 grams (1.2 moles) of sodium hydrogen sulfide in 150 ml of water and simultaneously 210 grams of a concentrated aqueous solution of ammonia (3.0 moles). The mixture was held for a further two hours with stirring at 20° to 25° C. Two phases resulted. The heavier, which contained the 2,2-pentamethylene-4,5-dimethlyl-thiazoline-(3) formed was separated and distilled. The thiazoline had a boiling point of 98° to 102° C. at 7 mbar. The yield was 127 grams, corresponding to 70% based on the 3-bromobutanone-(2) employed.

What is claimed is:

1. A process for preparing a thiazoline-(3) compound of the formula

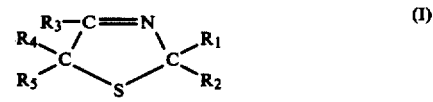

in which $R_1$, $R_2$, $R_3$, $R_4$ and $R_5$ individually are hydrogen, alkyl, alkenyl, cycloalkyl, cycloalkenyl, aryl, alkaryl or aralkyl or $R_1$ and $R_2$ are joined together, $R_3$ and $R_4$ are joined together, $R_3$ and $R_5$ are joined together or $R_4$ and $R_5$ are joined together and form with the carbon atom or atoms of the thiazoline ring to which they are connected a ring, said process comprising reacting (1) an oxo compound having a halogen atom on the carbon adjacent to the carbonyl group and having the formula

where X is halogen, (2) an oxo compound of the formula

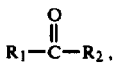
(III)

(3) a metal or ammonium hydrogen sulfide and (4) ammonia.

2. The process of claim 1 wherein $R_1$, $R_2$, $R_3$, $R_4$ and $R_5$ individually are hydrogen, alkyl of 1 to 18 carbon atoms, alkenyl of 2 to 8 carbon atoms, cycloalkyl of 3 to 12 carbon atoms, cycloalkenyl of 3 to 12 carbon atoms, phenyl, alkylphenyl with 1 to 6 carbon atoms in the alkyl group or phenalkyl with 1 to 6 carbon atoms in the alkyl group, or $R_1$ and $R_2$ together, $R_3$ and $R_4$ together, $R_3$ and $R_5$ together or $R_4$ and $R_5$ together are alkylene of 3 to 12 carbon atoms.

3. The process of claim 2 wherein (3) is an alkali metal, an alkaline earth metal or ammonium hydrogen sulfide.

4. The process of claim 3 wherein (3) is sodium hydrogen sulfide, potassium hydrogen sulfide or ammonium hydrogen sulfide.

5. The process of claim 2 wherein $R_1$, $R_2$, $R_3$, $R_4$ and $R_5$ individually are hydrogen, alkyl of 1 to 8 carbon atoms, alkenyl of 2 to 6 carbon atoms, cycloalkyl with 5 to 8 carbon atoms, cycloalkenyl with 5 to 8 carbon atoms, phenyl, alkylphenyl with 1 to 2 carbon atoms in the alkyl group, phenalkyl with 1 to 2 carbon atoms in the alkyl group or $R_1$ and $R_2$ together, $R_3$ and $R_4$ together, $R_3$ and $R_5$ together or $R_4$ and $R_5$ together are alkylene of 4 to 7 carbon atoms.

6. The process of claim 2 wherein $R_1$, $R_2$, $R_3$, $R_4$ and $R_5$ individually are hydrogen, alkyl of 1 to 3 carbon atoms, alkenyl of 2 to 4 carbon atoms, cycloalkyl of 5 to 6 carbon atoms or phenyl or $R_1$ and $R_2$ together, $R_3$ and $R_4$ together, $R_3$ and $R_5$ together or $R_4$ and $R_5$ together are alkylene of 4 to 7 carbon atoms.

7. The process of claim 6 wherein $R_1$ individually is hydrogen or alkyl of 1 to 3 carbon atoms, $R_2$ individually is hydrogen or alkyl of 1 to 2 carbon atoms, $R_3$ is hydrogen, methyl or phenyl, $R_4$ is hydrogen or methyl, $R_5$ is hydrogen or methyl or $R_1$ and $R_2$ together are pentamethylene.

8. The process of claim 1 wherein there are simultaneously added to a mixture of the oxo compound (2) and the ammonium or metal hydrogen sulfide (3) the halogen substituted oxo compound (1) and the ammonia (4).

9. A process according to claim 2 wherein at least one of reactant (II) and reactant (III) is a ketone.

10. A process according to claim 2 wherein $R_3$ is other than hydrogen.

11. A process according to claim 2 wherein the process consists essentially of reacting (1), (2), (3) and (4).

12. A process according to claim 11 wherein X is chlorine or bromine.

13. A process according to claim 1 wherein X is chlorine or bromine.

14. A process according to claim 1 wherein the process consists essentially of reacting (1), (2), (3) and (4).

* * * * *